US009795283B2

(12) United States Patent
Eto (10) Patent No.: US 9,795,283 B2
(45) Date of Patent: Oct. 24, 2017

(54) ENDOSCOPIC TREATMENT DEVICE (71) Applicant: OLYMPUS CORPORATION, Tokyo (JP)

(72) Inventor: Hirofumi Eto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/926,996

(22) Filed: Oct. 29, 2015

(65) Prior Publication Data
US 2016/0045100 A1 Feb. 18, 2016

Related U.S. Application Data (63) Continuation of application No. PCT/JP2014/079835, filed on Nov. 11, 2014.

(30) Foreign Application Priority Data

Nov. 21, 2013 (JP) ................................ 2013-240892

(51) Int. Cl.
*A61B 1/00* (2006.01)
*A61B 17/32* (2006.01)
(Continued)

(52) U.S. Cl.
CPC .......... *A61B 1/018* (2013.01); *A61B 1/00087* (2013.01); *A61B 1/00128* (2013.01);
(Continued)

(58) Field of Classification Search
CPC ............ A61B 1/00087; A61B 1/00133; A61B 1/00137; A61B 1/0014; A61B 1/012;
(Continued)

(56) References Cited

U.S. PATENT DOCUMENTS 8,197,396 B2 * 6/2012 Hiraoka ............. A61B 1/00137
600/104
2001/0004676 A1 * 6/2001 Ouchi ................ A61B 1/00133
600/106
(Continued)

FOREIGN PATENT DOCUMENTS

JP 2005198868 A 7/2005
JP 2007289673 A 11/2007
(Continued)

OTHER PUBLICATIONS

Mar. 3, 2015 International Search Reort issued in International Patent Application No. PCT/JP2014/079835.

*Primary Examiner* — Ryan Henderson
(74) *Attorney, Agent, or Firm* — Oliff PLC (57) ABSTRACT

An endoscopic treatment device includes an insertion unit, a manipulation unit provided at a proximal end portion of the insertion unit, and a manipulation unit attachment mechanism attaching the manipulation unit to an insertion port of a channel of an endoscope. The manipulation unit attachment mechanism has: a connection slider engaged with the insertion port by sliding in a first direction intersecting an axis of the insertion unit and disengaged from the insertion port by sliding in a second direction intersecting the axis; an insertion-port abutment part moving toward a proximal end by contacting with the insertion port; and a slider abutment part preventing sliding of the connection slider in the first direction when the insertion-port abutment part is located at a distal end side and permitting the sliding of the connection slider in the first direction when the insertion-port abutment part is located at a proximal end side.

6 Claims, 6 Drawing Sheets (51) Int. Cl.
  *A61B 1/018* (2006.01)
  *A61B 17/34* (2006.01)
  *A61B 17/00* (2006.01)

(52) U.S. Cl.
  CPC ...... *A61B 1/00137* (2013.01); *A61B 17/3478* (2013.01); *A61B 1/00073* (2013.01); *A61B 2017/0034* (2013.01); *A61B 2017/00292* (2013.01); *A61B 2017/00296* (2013.01); *A61B 2017/00318* (2013.01)

(58) Field of Classification Search
  CPC .............. A61B 1/018; A61B 17/00234; A61B 17/0218; A61B 17/0469; A61B 17/12013; A61B 17/1285; A61B 17/29; A61B 17/320016; A61B 17/32002; A61B 17/320024; A61B 17/320028; A61B 17/320032; A61B 2017/00292; A61B 2017/00296; A61B 2017/0034
  USPC ....... 600/102, 104, 106, 107, 153, 154, 566, 600/567; 606/167, 170, 172, 181, 185, 606/205
  See application file for complete search history.

(56) References Cited

U.S. PATENT DOCUMENTS

| | | | |
|---|---|---|---|
| 2003/0028096 A1* | 2/2003 | Niwa | A61B 1/00128 600/424 |
| 2005/0182292 A1 | 8/2005 | Suzuki | |
| 2007/0276180 A1* | 11/2007 | Greenburg | A61B 1/00128 600/106 |
| 2008/0208214 A1* | 8/2008 | Sato | A61B 17/1114 606/139 |
| 2008/0242925 A1* | 10/2008 | Suda | A61B 1/00137 600/104 |
| 2009/0062830 A1* | 3/2009 | Hiraoka | A61B 10/0233 606/185 |
| 2009/0069822 A1* | 3/2009 | Takahashi | A61B 17/064 606/139 |
| 2010/0010508 A1* | 1/2010 | Takahashi | A61B 17/064 606/139 |
| 2010/0010520 A1* | 1/2010 | Takahashi | A61B 17/064 606/157 |
| 2010/0022826 A1* | 1/2010 | Akahoshi | A61B 17/2909 600/104 |
| 2010/0228084 A1 | 9/2010 | Sato et al. | |
| 2012/0029278 A1* | 2/2012 | Sato | A61B 17/00234 600/104 |
| 2012/0116248 A1* | 5/2012 | McWeeney | A61B 10/0283 600/567 |

FOREIGN PATENT DOCUMENTS

| | | |
|---|---|---|
| JP | 2010269126 A | 12/2010 |
| JP | 2011212450 A | 10/2011 |
| JP | 2013188416 A | 9/2013 |

* cited by examiner

ENDOSCOPIC TREATMENT DEVICE

This application is a continuation application based on PCT Patent Application No. PCT/JP2014/079835, filed Nov. 11, 2014, whose priority is claimed on Japanese Patent Application No. 2013-240892, filed on Nov. 21, 2013. The contents of both the PCT Patent Application and the Japanese Patent Application are incorporated herein by reference.

BACKGROUND OF THE INVENTION

Field of the Invention

The present invention relates to an endoscopic treatment device for performing treatment on tissue.

Description of Related Art

Conventionally, various treatments are carried out simultaneously with observation with an endoscope by inserting an endoscopic treatment device into a channel formed in the endoscope. As this type of endoscopic treatment device, an endoscopic treatment device described in, for instance, Japanese Unexamined Patent Application, First Publication No. 2007-289673 is known.

This endoscopic treatment device is equipped with a forceps body (insertion unit) that is inserted into the channel of the endoscope to perform an actual treatment, and a manipulation unit body (manipulation unit) that performs positioning of the forceps body to the channel and opening/closing of forceps cups to be described below. The forceps body is equipped with an outer sheath that is inserted into the channel of the endoscope, a coil sheath that is movably disposed inside the outer sheath in a direction of an axis of the outer sheath, a pair of forceps cups that are openably and closably attached to a distal end of the coil sheath, and a manipulation wire that opens/closes the forceps cups. The manipulation wire is movably disposed inside the coil sheath in a direction of an axis of the coil sheath and is connected to the forceps cups. The manipulation wire opens/closes the forceps cups when moved in the direction of the axis.

The manipulation unit body is equipped with an endoscope coupling that is fixed to an insertion port of the channel of the endoscope and is connected to a proximal end portion of the outer sheath, a slider that is movably attached to the endoscope coupling in a direction of an axis of the proximal end portion of the outer sheath and is connected to a proximal end portion of the coil sheath, and a button that is movably attached to the slider in a direction of an axis of the proximal end portion of the coil sheath and is connected to a proximal end portion of the manipulation wire. The endoscope coupling has a cylindrical connecting member that is assembled to the insertion port of the channel of the endoscope. A locking member (connection slider) is slidably connected to a distal end portion of the connecting member in a direction orthogonal to an axis of the connecting member. The connecting member is fixed to the insertion port of the endoscope via an adapter forceps plug in a liquid-tight state with the adapter forceps plug fitted into the insertion port of the endoscope.

A manipulation unit support pipe member is attached to the connecting member along the axis. The manipulation unit support pipe member is fitted onto the outer sheath.

A method of collecting tissue of a patient using the endoscopic treatment device configured in this way is as follows. The endoscopic treatment device is inserted into the channel of the endoscope from the insertion port. To be specific, the adapter forceps plug is fitted into the insertion port, and the connecting member is further moved toward the insertion port, and fitted into the adapter forceps plug. In this state, the locking member is moved in the direction orthogonal to the axis of the connecting member. Thereby, the endoscopic treatment device is fixed to be prevented from being carelessly detached from the endoscope.

SUMMARY OF THE INVENTION

According to a first aspect of the present invention, an endoscopic treatment device includes: an insertion unit configured to be insertable into a channel of an endoscope; a manipulation unit provided at a proximal end portion of the insertion unit; and a manipulation unit attachment mechanism provided at the manipulation unit, and configured to removably attach the manipulation unit to an insertion port provided at a proximal end portion of the channel of the endoscope when the insertion unit is inserted into the channel of the endoscope. The manipulation unit attachment mechanism has: a connection slider configured to be engaged with the insertion port by sliding in a first direction intersecting an axis of the insertion unit in a state in which the manipulation unit is attached to the insertion port and be disengaged from the insertion port by sliding in a second direction intersecting the axis of the insertion unit; an insertion-port abutment part configured to be movable relative to the manipulation unit in a direction of the axis of the insertion unit and move toward a proximal end of the insertion unit in the direction of the axis of the insertion unit by coming into contact with the insertion port in the state in which the manipulation unit is attached to the insertion port; and a slider abutment part that is provided at the insertion-port abutment part and that is configured to come into contact with the connection slider to prevent sliding of the connection slider in the first direction when the insertion-port abutment part is located at a distal end side of the insertion unit in the direction of the axis of the insertion unit, and do not come into contact with the connection slider to permit the sliding of the connection slider in the first direction when the insertion-port abutment part is located at a proximal end side of the insertion unit in the direction of the axis of the insertion unit.

According to a second aspect of the present invention, the endoscopic treatment device according to the first aspect of the present invention may further include a biasing member configured to bias the insertion-port abutment part toward the distal end side.

According to a third aspect of the present invention, in the endoscopic treatment device according to the second aspect of the present invention, the connection slider may have a locking hole formed to pass through the connection slider in the direction of the axis. The slider abutment part that has moved toward the distal end side may be inserted into the locking hole of the connection slider that has slid in the second direction, and thereby the connection slider may be prevented from sliding in the first direction.

According to a fourth aspect of the present invention, in the endoscopic treatment device according to the third aspect of the present invention, the insertion-port abutment part may be formed in a tubular shape. A tubular groove may be formed in a support face of the manipulation unit, the support face being exposed at a distal end side of the manipulation unit. A proximal end side of the insertion-port abutment part may be inserted into the tubular groove.

According to a fifth aspect of the present invention, in the endoscopic treatment device according to the fourth aspect of the present invention, the manipulation unit may include a support tube that extends in the direction of the axis and has an outer diameter such that the support tube is insertable into the insertion port. The insertion unit may be inserted into the support tube.

According to a sixth aspect of the present invention, in the endoscopic treatment device according to the fifth aspect of the present invention, the insertion unit may have: a sheath; and a needle tube configured to be advanceably and retractably inserted into the sheath.

DETAILED DESCRIPTION OF THE INVENTION

Figure 1:
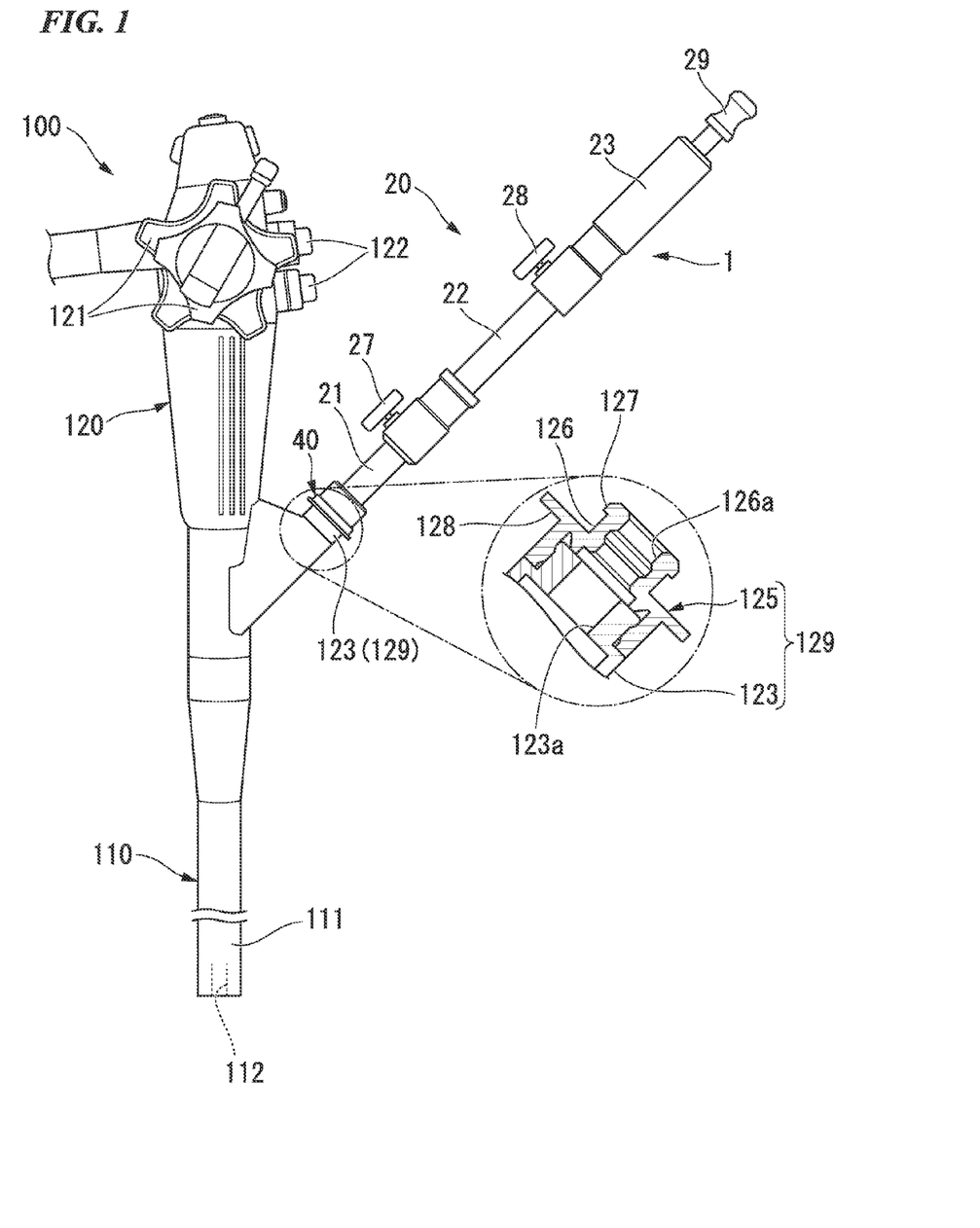
FIG. 1 is an illustrative view of a puncture needle according to an embodiment of the present invention and an endoscope used along with the puncture needle.
Figure 2:
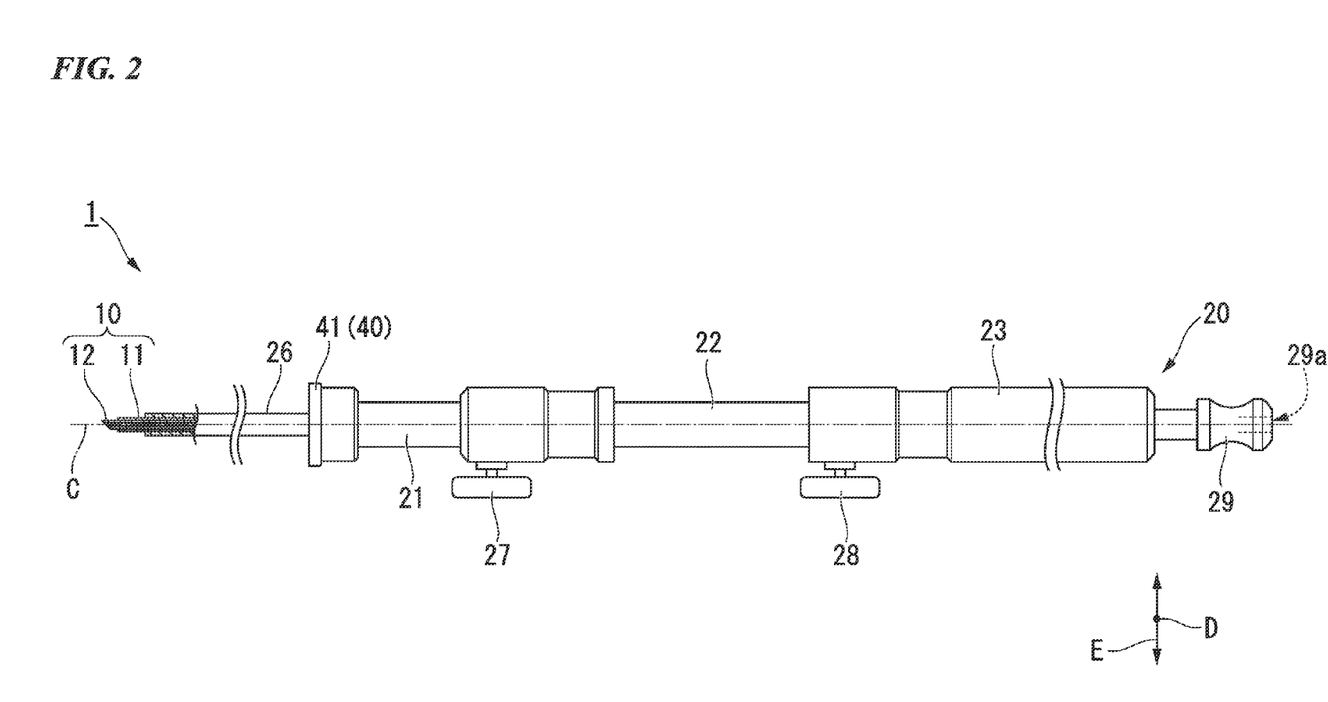
FIG. 2 is a side view in which a part of the puncture needle is cut away.

Hereinafter, an endoscopic treatment device according to an embodiment of the present invention will be described, for instance, as a puncture needle (suction biopsy needle) with reference to FIGS. 1 to 10. As shown in FIGS. 1 and 2, the puncture needle 1 according to the present embodiment is used along with a well-known endoscope 100. The puncture needle 1 is equipped with a long insertion unit 10 that is insertable into a channel 112 of the endoscope 100, a manipulation unit 20 that is provided at a proximal end portion of the insertion unit 10, and a manipulation unit attachment mechanism 40 that is provided at a distal end side of the manipulation unit 20.

First, an endoscope 100 used along with the puncture needle 1 will be described. Hereinafter, the case in which the endoscope is a so-called direct-view endoscope with which an area located ahead of an endoscope insertion unit is observable will be described as an example. The constitution of the endoscope is not limited thereto, and the endoscope may be a so-called side-view endoscope with which an area beside the endoscope insertion unit is observable. Further, as the endoscope, a so-called ultrasonic endoscope in which observation based on visible light as well as observation based on ultrasonic waves is possible may be used.

The endoscope 100 has a well-known constitution. As shown in FIG. 1, the endoscope 100 is equipped with an endoscope insertion unit 110 that is flexible and long, and an endoscope manipulation unit 120 that is provided at a proximal end portion of the endoscope insertion unit 110. A bending part 111 that can be bent is provided at a distal end side of the endoscope insertion unit 110. A manipulation wire (not shown) attached to the bending part 111 is inserted into the endoscope insertion unit 110 to extend up to the endoscope manipulation unit 120. Although not shown, an imaging unit having a light guide and a charge coupled device (CCD) is provided at a distal end face of the endoscope insertion unit 110 in an exposed state. The aforementioned channel 112 is formed in the endoscope insertion unit 110 along the endoscope insertion unit 110. A distal end portion of the channel 112 is open to the distal end face of the endoscope insertion unit 110.

Angle knobs 121 for manipulating the aforementioned manipulation wire, and switches 122 for operating a light source (not shown), a monitor (not shown), the aforementioned imaging unit (not shown), and so on are provided on the endoscope manipulation unit 120. By manipulating the angle knobs 121, the bending part 111 can be bent in a desired direction. A forceps insertion port 123 that is formed of a metal such as stainless steel and has an insertion hole 123a is provided at a distal end side of the endoscope manipulation unit 120. The forceps insertion port 123 is provided at a proximal end portion of the channel 112. The insertion hole 123a of the forceps insertion port 123 communicates with the channel 112.

An adapter forceps plug 125 formed of an elastic material such as a rubber is fitted onto the forceps insertion port 123. The adapter forceps plug 125 has an adapter body 126 formed in a tubular shape, a locking part 127 provided at a proximal end portion of an outer circumferential surface of the adapter body 126, and a flange 128 provided at a longitudinal middle portion of the outer circumferential surface of the adapter body 126. The forceps insertion port 123 and the adapter forceps plug 125 constitute an insertion port 129. An insertion hole 126a of the adapter body 126 has a slightly smaller inner diameter than the insertion hole 123a of the forceps insertion port 123. The adapter forceps plug 125 is provided with a check valve (not shown) that prevents a liquid from flowing from the side of the forceps insertion port 123 through the insertion hole 126a to the outside.

Next, the puncture needle 1 will be described. As shown in FIG. 2, the insertion unit 10 has a sheath 11 and a needle tube 12 that is advanceably and retractably inserted into the sheath 11. The sheath 11 is formed with such a diameter that it can be inserted into the channel 112 of the endoscope 100. The sheath 11 may be formed of a polyether ether ketone (PEEK), a fluorine resin, an olefin resin, a urethane resin, a nylon (polyamide) resin, or a coil of a metal. The needle tube 12 is formed in a tubular shape. A distal end of the needle tube 12 is cut off to be inclined with respect to an axis (central axis) C of the sheath 11, and thereby is sharply formed to be able to pierce biological tissue. A material of which the needle tube 12 is formed is preferably a material that has flexibility and elasticity by which it is easily restored to a linear state even if curved by an external force. Such a material may include an alloy material such as a stainless alloy, a nickel-titanium alloy, and a cobalt-chromium alloy.

Figure 3:
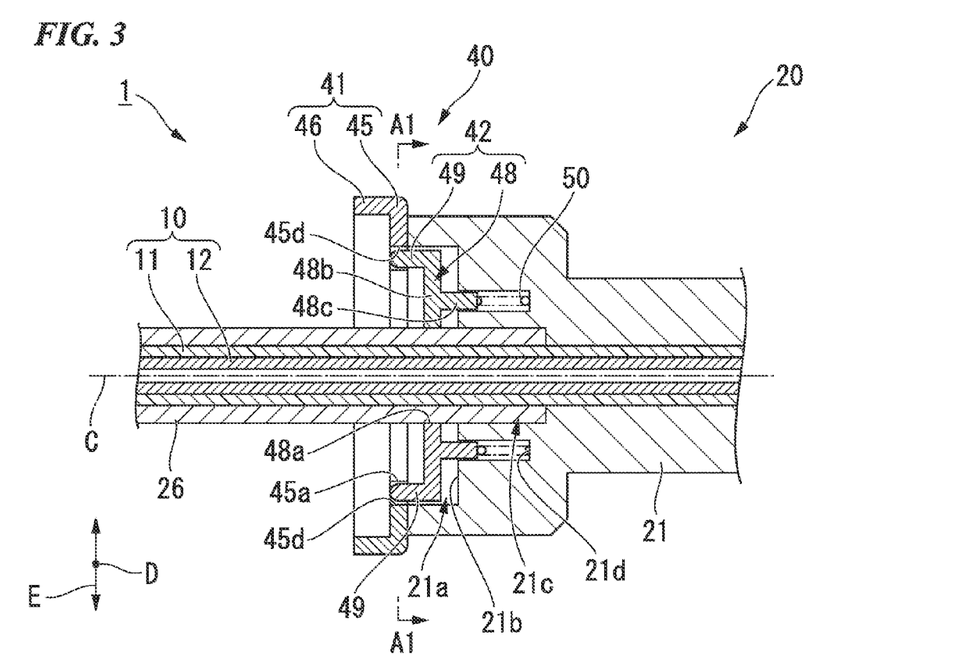
FIG. 3 is a side sectional view of principal parts of the puncture needle.

As shown in FIGS. 2 and 3, the manipulation unit 20 has a connecting member 21 that is formed in a cylindrical shape, a slider receiver 22 that is movably inserted into a proximal end portion of the connecting member 21 in a direction of the axis C, and a slider 23 that is attached to a proximal end portion of the slider receiver 22. As shown in FIG. 3, a large-diameter recess 21a recessed toward the proximal end of the connecting member 21 is formed in a center portion of a distal end face of the connecting member 21 on the same axis as the axis C. A support face 21b that is the bottom of the large-diameter recess 21a is exposed to the outside at a distal end side thereof. A small-diameter recess 21c having a smaller diameter than the large-diameter recess 21a is formed in the center of the support face 21b of the large-diameter recess 21a to be recessed toward the proximal end of the connecting member 21 on the same axis as the axis C. A cylindrical tubular groove 21d is formed in the support face 21b of the large-diameter recess 21a at a radial outer side relative to the small-diameter recess 21c. The connecting member 21 is formed in one body of a well-known resin material.

A proximal end portion of a manipulation unit support pipe member (support tube) 26 formed of a metal such as stainless steel is engaged with the small-diameter recess 21c. The manipulation unit support pipe member 26 is fixed to the connecting member 21 by, for instance, an adhesive (not shown). The manipulation unit support pipe member 26 extends in the direction of the axis C. The insertion unit 10 is advanceably and retractably inserted into the manipulation unit support pipe member 26 and into the connecting member 21. An outer diameter of the manipulation unit support pipe member 26 is slightly smaller than the inner diameter of the insertion hole 123a of the forceps insertion port 123 of the endoscope 100. The manipulation unit support pipe member 26 can be inserted into the insertion port 129.

As shown in FIG. 2, a screw 27 provided between the connecting member 21 and the slider receiver 22 is fastened. Thereby, in a state in which positions of the connecting member 21 and the slider receiver 22 in the direction of the axis C are adjusted, the connecting member 21 and the slider receiver 22 can be fixed. A slider groove (not shown) is formed in a proximal end portion of an outer circumferential surface of the slider receiver 22 along the axis C. The slider receiver 22 is fixed to a proximal end portion of the sheath 11. The needle tube 12 is advanceably and retractably inserted into the slider receiver 22. The slider 23 is fitted onto the slider groove of the slider receiver 22, and is attached to be movable relative to the slider receiver 22 in the direction of the axis C. A screw 28 provided between the slider receiver 22 and the slider 23 is fastened. Thereby, in a state in which positions of the slider receiver 22 and the slider 23 in the direction of the axis C are adjusted, the slider receiver 22 and the slider 23 can be fixed. A proximal end portion of the needle tube 12 is fixed to the slider 23, and a tube passage of the needle tube 12 communicates with an opening 29a of a connecting port 29 provided at a proximal end portion of the slider 23. The opening 29a of the connecting port 29 is configured in such a way that, for instance, a well-known syringe can be attached to or detached from the opening 29a.

As shown in FIGS. 2 and 3, the aforementioned manipulation unit attachment mechanism 40 for removably attaching the manipulation unit 20 to the insertion port 129 when the insertion unit 10 is inserted into the channel 112 of the endoscope 100 is provided at a distal end portion of the connecting member 21. The manipulation unit attachment mechanism 40 has a connection slider 41 that is provided to be slidable relative to the connecting member 21 in a cross direction D intersecting the axis C, and a regulating member 42 that is provided inside the large-diameter recess 21a of the connecting member 21.

Figure 4:
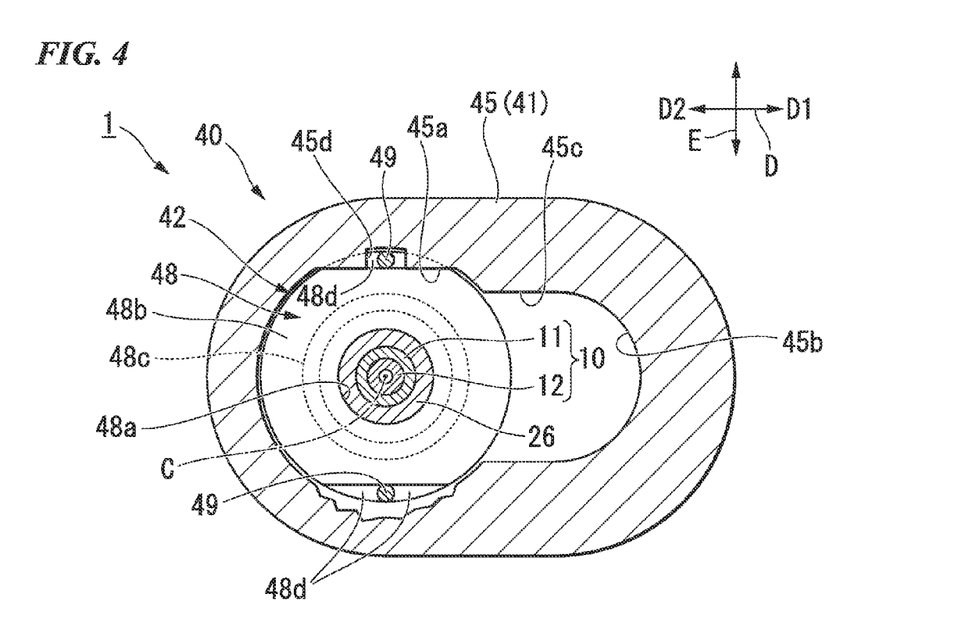
FIG. 4 is a sectional view taken along a section line A1-A1 of FIG. 3.

As shown in FIGS. 3 and 4, the connection slider 41 is equipped with a slider body 45 that is formed in a plate shape extending in a direction perpendicular to the axis C, and a reinforcement member 46 that extends from an edge of the slider body 45 toward a distal end of the slider body 45. Further, it is shown in FIG. 4 that a part of the slider body 45 is cut off. The slider body 45 is formed with a large-diameter hole 45a, a small-diameter hole 45b that has a smaller inner diameter than the large-diameter hole 45a, and a communication hole 45c that causes the large-diameter hole 45a and the small-diameter hole 45b to communicate with each other. When viewed in the direction of the axis C (thickness direction of the slider body 45) shown in FIG. 4, the slider body 45 is formed with locking holes 45d (the locking hole 45d on one side is not shown) that are recessed from respective edges of the large-diameter hole 45a in a width direction E orthogonal to the cross direction D and pass through the slider body 45 in the direction of the axis C. Portions of the large-diameter hole 45a other than the pair of the locking holes 45d have a larger inner diameter in the width direction E than an outer diameter of the locking part 127 of the insertion port 129 of the endoscope 100. The inner diameter of the small-diameter hole 45b in the width direction E is smaller than the outer diameter of the locking part 127 of the endoscope 100, and is larger than an outer diameter of the adapter body 126. Although not shown, the connecting member 21 has a slider groove formed in a face orthogonal to the axis C. Due to this slider groove, the connection slider 41 is regulated to slide relative to the connecting member 21 only in the cross direction D.

Figure 5:
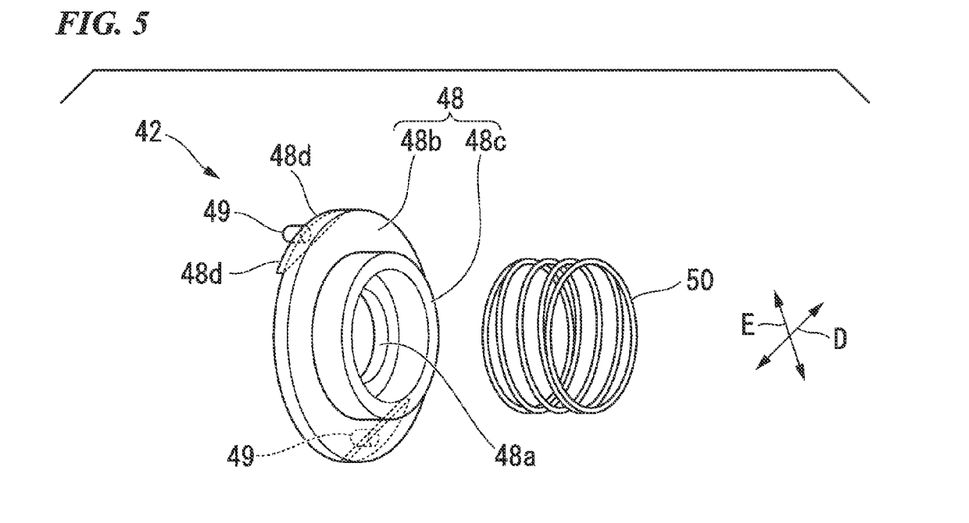
FIG. 5 is an exploded perspective view of a regulating member and a spring member of the puncture needle.

As shown in FIGS. 3 to 5, the regulating member 42 is equipped with an insertion-port abutment part 48 that is formed in a cylindrical shape, and a pair of slider abutment parts 49 that are provided on a distal end face of the insertion-port abutment part 48. The insertion-port abutment part 48 has an abutment part body 48b that is formed in a disc shape and has a through-hole 48a formed in the center thereof, and a cylindrical guide wall 48c. The guide wall 48c is provided on a proximal end face of the abutment part body 48b to protrude toward a proximal end thereof. The guide wall 48c is insertable into the tubular groove 21d of the connecting member 21. The slider abutment parts 49 are each formed in a rod shape extending in the direction of the axis C, and are provided at respective edges of a distal end face of the abutment part body 48b to interpose the through-hole 48a therebetween. The pair of slider abutment parts 49 have the same pitch as the pair of locking holes 45d. Supports 48d are provided on the distal end face of the abutment part body 48b at one side (second direction) D1 and the other side (first direction) D2 of the cross direction D of the slider abutment parts 49. Lengths of the supports 48d in the direction of the axis C are shorter than those of the slider abutment parts 49 in the direction of the axis C.

The slider body 45 and the reinforcement member 46 constituting the connection slider 41 are integrally formed of, for instance, a resin material such as polycarbonate or polyacetal. Also, the insertion-port abutment part 48 and the pair of slider abutment parts 49 constituting the regulating member 42 are integrally formed of, for instance, a resin material such as polycarbonate or polyacetal. A spring member (biasing member) 50 such as a helical spring is disposed in the tubular groove 21d of the connecting member 21. A proximal end portion of the spring member 50 is locked on the bottom of the tubular groove 21d, and a distal end portion of the spring member 50 is locked on a proximal end face of the guide wall 48c of the regulating member 42. As the guide wall 48c is inserted into the tubular groove 21d, the spring member 50 is compressed in the direction of the axis C, and biases the guide wall 48c of the insertion-port abutment part 48 toward a distal end thereof. That is, by expanding and contracting the spring member 50, the regulating member 42 is movable relative to the connecting member 21 in the direction of the axis C. The manipulation unit support pipe member 26 is inserted into the through-hole 48a of the regulating member 42, and the large-diameter hole 45a, the small-diameter hole 45b and the communication hole 45c of the connection slider 41.

As shown in FIGS. 3 and 4, when the connection slider 41 slides relative to the connecting member 21 to the one side D1 of the cross direction D, the large-diameter hole 45a of the connection slider 41 is disposed on the axis C, and the regulating member 42 is biased toward the distal end by the spring member 50. Thereby, the slider abutment parts 49 of the regulating member 42 which have moved toward the distal end are inserted into the respective locking holes 45d of the connection slider 41. As the slider abutment parts 49 come into contact with respective edges of the locking holes 45d, the slider abutment parts 49 are locked on the connection slider 41 in the cross direction D, and the connection slider 41 is prevented from sliding relative to the regulating member 42, i.e. the connecting member 21, toward the other side D2 of the cross direction D. At this time, the distal end faces of the supports 48d come into contact with proximal end faces of the edges of the locking holes 45d, and thereby the regulating member 42 does not move toward the distal end beyond the connection slider 41.

Next, an operation of the puncture needle 1 constituted as described above will be described. Hereinafter, a biopsy treatment for collecting target tissue of a lesion located deep in a lung will be described as an example. When a user manipulates the switch 122 of the endoscope 100 to operate the light source, illuminating light emitted from the light source is guided to the light guide to illuminate an area located ahead of the endoscope insertion unit 110. An image acquired ahead of the endoscope insertion unit 110 by the imaging unit is displayed on the monitor. The user inserts the endoscope insertion unit 110 of the endoscope 100 into the body of a patient while checking the image displayed on the monitor. The user continues to insert the endoscope insertion unit 110 while manipulating the angle knobs 121 to appropriately bend the bending part 111. The endoscope insertion unit 110 is held in a state in which the distal end face of the endoscope insertion unit 110 is kept opposite to a region subjected to biopsy.

Subsequently, the screw 27 is fastened in a state in which the slider receiver 22 is moved (pulled back) toward the proximal end with respect to the connecting member 21, and thus fixes the connecting member 21 and the slider receiver 22. The screw 28 is fastened in a state in which the slider 23 is pulled back with respect to the slider receiver 22 to house the needle tube 12 in the sheath 11, and thus fixes the slider receiver 22 and the slider 23. At this time, a stylet is preferably inserted into the tube passage of the needle tube 12 from the opening 29a of the connecting port 29. The user grasps the endoscope manipulation unit 120 with one hand, and inserts the sheath 11 of the puncture needle 1 and the manipulation unit support pipe member 26 into the insertion hole 126a of the adapter forceps plug 125 of the endoscope 100 and the insertion hole 123a of the forceps insertion port 123. The sheath 11 displaces the check valve of the adapter forceps plug 125. A space between the adapter forceps plug 125 and the manipulation unit support pipe member 26 is sealed in a watertight way by an elastic force of the adapter forceps plug 125. Since the outer diameter of the manipulation unit support pipe member 26 and the inner diameter of the insertion hole 123a of the forceps insertion port 123 are set as described above, the manipulation unit support pipe member 26 slides in the insertion hole 123a, and is reliably supported by the forceps insertion port 123.

The space between the adapter forceps plug 125 and the manipulation unit support pipe member 26 is sealed in a watertight way, and the forceps insertion port 123 and the manipulation unit support pipe member 26 slide. For this reason, due to a frictional force applied between the adapter forceps plug 125 and the manipulation unit support pipe member 26 and a frictional force applied between the forceps insertion port 123 and the manipulation unit support pipe member 26, the puncture needle 1 is disposed with respect to the insertion port 129 at an arbitrary position of the sheath 11 in the direction of the axis C. When the manipulation unit support pipe member 26 is displaced (pushed) toward the distal end with respect to the adapter forceps plug 125, the manipulation unit support pipe member 26 moves toward the proximal end due to the elastic force of the adapter forceps plug 125 in some cases. In this state, the edges of the locking holes 45d come into contact with the slider abutment parts 49. Thereby, the connection slider 41 is prevented from sliding relative to the connecting member 21 toward the other side D2 of the cross direction D.

Figure 6:
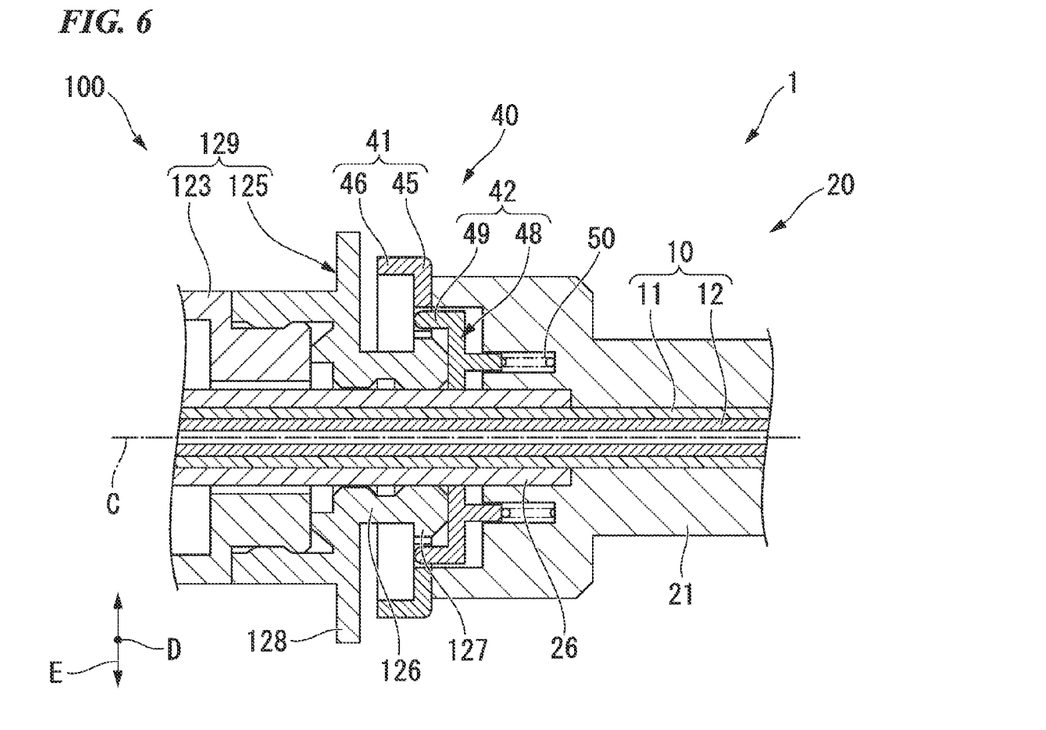
FIG. 6 is a sectional view showing an operation of the puncture needle.
Figure 7:
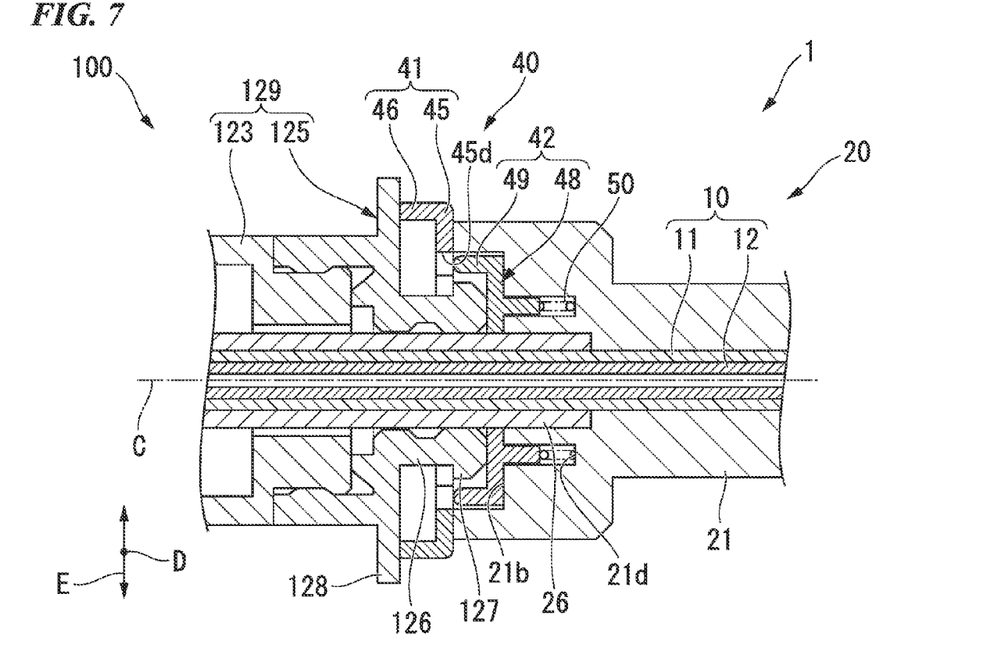
FIG. 7 is a sectional view showing an operation of the puncture needle.

When the puncture needle 1 is further pushed with respect to the insertion port 129 to bring the insertion port 129 and the manipulation unit 20 relatively close to each other, the insertion-port abutment part 48 of the regulating member 42 comes into contact with a proximal end portion of the adapter forceps plug 125 as shown in FIG. 6. When the puncture needle 1 is further pushed against the biasing force of the spring member 50, as shown in FIG. 7, the spring member 50 is contracted in the direction of the axis C, and the regulating member 42 is displaced (located) toward the proximal end with respect to the connecting member 21. The slider abutment parts 49 of the regulating member 42 are drawn from the respective locking holes 45d of the connection slider 41 and are separated from the connection slider 41, and the slider abutment parts 49 allow the connection slider 41 to slide toward the other side D2 of the cross direction D without locking the connection slider 41. At this time, the manipulation unit 20 is disposed at a predetermined position which is on the axis of the channel 112 with respect to the insertion port 129 and at which the connection slider 41 is disposed between the flange 128 and the locking part 127 of the adapter forceps plug 125 in the direction of the axis C. The connection slider 41 slides relative to the connecting member 21 toward the one side D1 of the cross direction D, and the insertion port 129 and the connection slider 41 are not engaged. The tubular groove 21d is formed in the support face 21b of the connecting member 21, and the insertion-port abutment part 48 formed in the cylindrical shape is inserted into the tubular groove 21d. Movement of the insertion-port abutment part 48 in the direction of the axis C is guided throughout the circumference by the tubular groove 21d, and is thereby stabilized.

Figure 8:
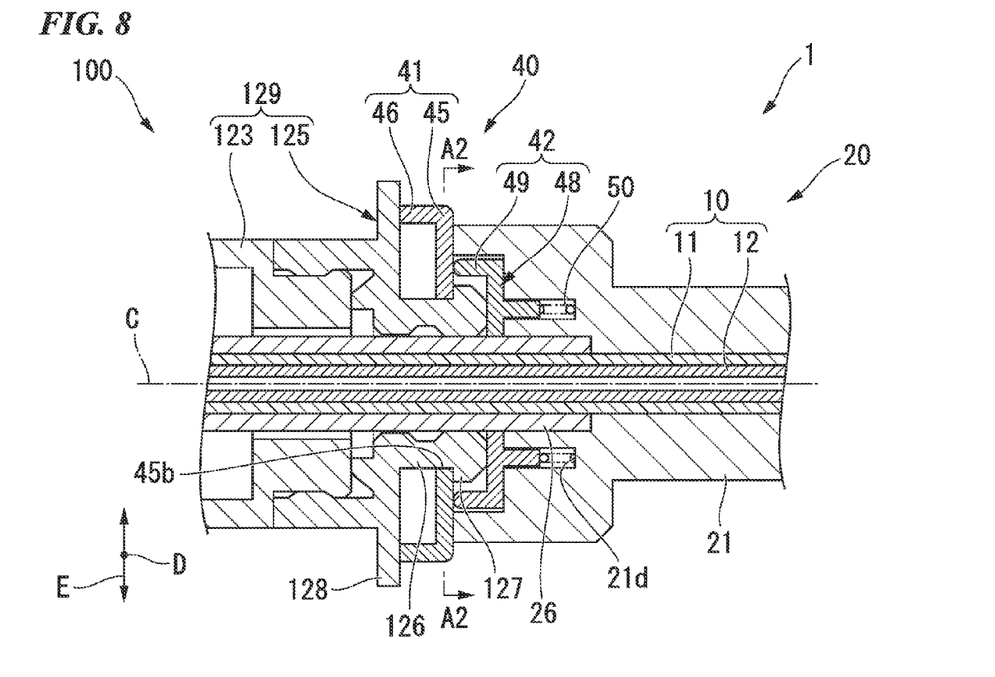
FIG. 8 is a sectional view showing an operation of the puncture needle.
Figure 9:
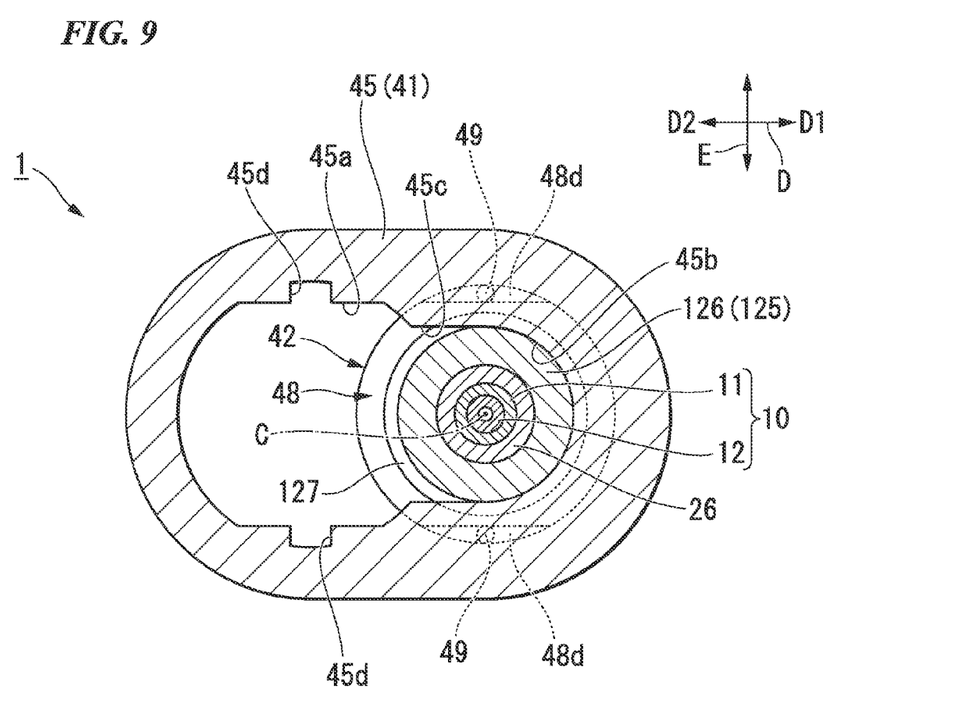
FIG. 9 is a sectional view taken along a section line A2-A2 of FIG. 8.

Here, as shown in FIGS. 8 and 9, when a user slides the connection slider 41 toward the other side D2 of the cross direction D relative to the connecting member 21, the small-diameter hole 45b of the connection slider 41 is disposed on the axis C, the connection slider 41 is disposed between the flange 128 and the locking part 127 of the adapter forceps plug 125, and the manipulation unit attachment mechanism 40 can move relative to the insertion port 129 toward neither the distal end nor the proximal end due to the flange 128 and the locking part 127 (can be engaged). As the manipulation unit support pipe member 26 slides in the insertion hole 123a of the forceps insertion port 123, the manipulation unit attachment mechanism 40 cannot move relative to the insertion port 129 even in a radial direction, and thus is engaged with the insertion port 129.

Figure 10:
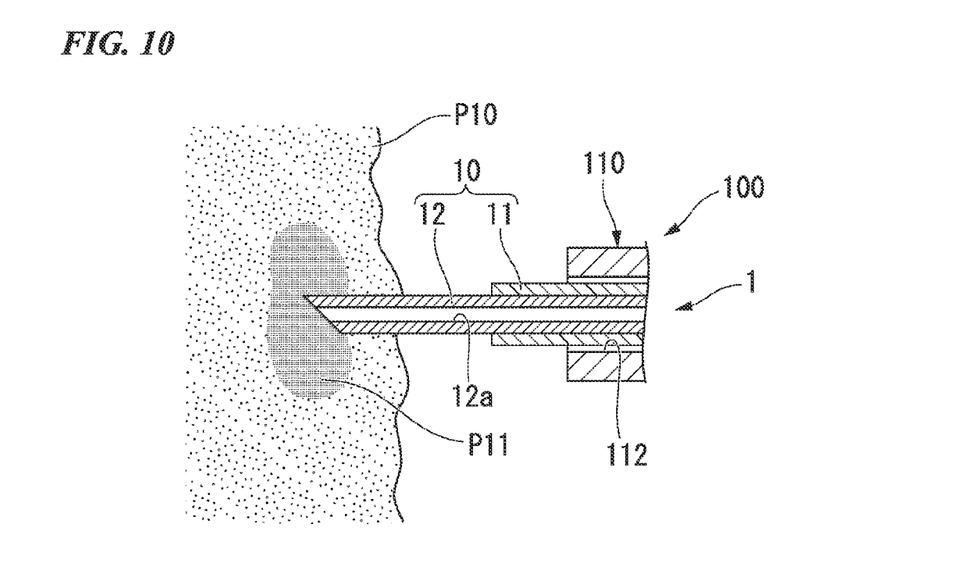
FIG. 10 is a sectional view showing an operation of the puncture needle.

The user manipulates the manipulation unit 20 of the puncture needle 1 with the other hand, loosens the screw 27 to push the slider receiver 22 relative to the connecting member 21, and as shown in FIG. 10, causes the sheath 11 to protrude from the distal end of the endoscope insertion unit 110. The user fastens the screw 27 to fix the connecting member 21 and the slider receiver 22. The user loosens the screw 28 to push the slider 23 relative to the slider receiver 22, and causes the needle tube 12 to protrude from the sheath 11. The user punctures tissue P10 with the distal end of the needle tube 12 and pushes the distal end of the needle tube 12 toward target tissue P11 for biopsy. The user extrudes tissue in the tube passage 12a of the needle tube 12 that is not a target for biopsy using a stylet, and draws the stylet from the needle tube 12.

The user attaches, for instance, a syringe to the opening 29a of the connecting port 29, and manipulates the syringe to suction an interior of the tube passage 12a. The target tissue P11 enters the tube passage 12a due to the suction. If necessary, agitation for piercing different regions of the target tissue P11 several times with the needle tube 12 to collect the target tissue P11 is performed. When a needed amount of the target tissue P11 is collected, the slider 23 is pulled back with respect to the slider receiver 22, and the needle tube 12 is housed in the sheath 11. Thereby, the needle tube 12 comes out of the tissue P10. The connection slider 41 is slid relative to the connecting member 21 toward the one side D1 of the cross direction D, and the engagement between the insertion port 129 and the connection slider 41, i.e. the manipulation unit attachment mechanism 40, is released. The user pulls the sheath 11 of the puncture needle 1 from the channel 112 of the endoscope 100, pulls the endoscope 100 from the patient, and performs a needed treatment, thereby terminating a series of procedures.

The user pushes the slider 23 against the slider receiver 22 of the puncture needle 1, and causes the needle tube 12 to protrude from the sheath 11. The user inserts the stylet into the tube passage 12a of the needle tube 12, and places the target tissue P11 in the tube passage 12a on a slide (not shown). The user diagnoses the target tissue P11 on the slide to perform the biopsy.

As described above, according to the puncture needle 1 of the present embodiment, the slider abutment parts 49 of the regulating member 42 are locked on the connection slider 41 that has slid toward the one side D1 of the cross direction D. Thereby, the connection slider 41 is prevented from sliding relative to the manipulation unit 20 toward the other side D2 of the cross direction D. The insertion unit 10 of the puncture needle 1 is inserted into the channel 112 of the endoscope 100, and the insertion port 129 and the manipulation unit 20 are brought relatively close to each other from the state in which the insertion-port abutment part 48 of the regulating member 42 is in contact with the insertion port 129. When the manipulation unit 20 is disposed at the aforementioned predetermined position, the insertion-port abutment part 48 moves relative to the manipulation unit 20 toward the proximal end. Along with the insertion-port abutment part 48, the slider abutment parts 49 also move toward the proximal end, and do not lock the connection slider 41. Here, the connection slider 41 is slid relative to the manipulation unit 20 toward the other side D2 of the cross direction D. Thereby, the connection slider 41 is engaged with the insertion port 129, and thus attaches the manipulation unit attachment mechanism 40 to the insertion port 129. In this way, the connection slider 41 cannot slide toward the other side D2 of the cross direction D until the manipulation unit 20 is disposed at the predetermined position with respect to the insertion port. For this reason, the user checks that the connection slider 41 is slid toward the other side D2 of the cross direction D, and thereby the manipulation unit 20 can be reliably fixed to the insertion port 129 of the endoscope 100. As a result, no situation in which the puncture needle 1 is unreliably fixed to the insertion port 129 occurs.

Further, as long as the manipulation unit 20 fixed to the insertion port 129 is not manipulated, a relative position between the endoscope insertion unit 110 of the endoscope 100 and the insertion unit 10 of the puncture needle 1 is not changed. For this reason, when the endoscope insertion unit 110 is held opposite to the tissue P10, the needle tube 12 does not come out of the tissue P10 without the intention of the user. As the puncture needle 1 comes out of the channel 112, the needle tube 12 does not damage an inner circumferential surface of the channel 112. In general, a member that interposes the insertion port therebetween in a radial direction may be provided for the manipulation unit of the puncture needle such that a direction around the axis of the insertion unit of the puncture needle is not changed relative to the channel of the endoscope. In this case, due to such a member, it is difficult to see a connection state between the insertion port and the manipulation unit. In the puncture needle 1 of the present embodiment, even when it is difficult to see the connection state between the insertion port 129 and the manipulation unit 20, the connection slider 41 can be slid toward the other side D2 of the cross direction D only when the manipulation unit 20 is disposed at the predetermined position. For this reason, the user checks that the connection slider 41 is slid toward the other side D2 of the cross direction D, and thereby can reliably fix the manipulation unit 20 to the insertion port 129 of the endoscope 100.

As the puncture needle 1 includes the spring member 50, the insertion-port abutment part 48 is surely biased toward the distal end, and the slider abutment parts 49 can be easily inserted into the locking holes 45d of the connection slider 41. The locking holes 45d are formed in the connection slider 41, and the slider abutment parts 49 that have moved toward the distal end can be inserted into the locking holes 45d. As the puncture needle 1 is constituted in this way, the connection slider 41 can be reliably prevented from sliding toward the other side D2 of the cross direction D with a simple constitution. The tubular groove 21d is formed in the support face 21b of the connecting member 21, and the insertion-port abutment part 48 formed in the cylindrical shape is inserted into the tubular groove 21d. Thus, the movement of the insertion-port abutment part 48 in the direction of the axis C can be stabilized.

Although an embodiment of the present invention has been described above in detail with reference to the drawings, the specific constitution is not limited to this embodiment, and also includes modifications, combinations, eliminations, and so on, of the constitution without departing from the scope of the present invention.

For example, in the embodiment, the insertion port 129 of the endoscope 100 is adapted to be made up of the forceps insertion port 123 and the adapter forceps plug 125. However, the insertion port may be adapted to be made up of only the forceps insertion port 123 without including the adapter forceps plug 125. In this case, the manipulation unit attachment mechanism 40 is directly attached to the forceps insertion port 123.

In the embodiment, the biasing member is adapted to be the spring member 50. However, the biasing member may be an elastic member such as rubber. Also, the puncture needle 1 may be configured not to include the spring member 50. This is because, if the puncture needle 1 is supported such that the slider abutment parts 49 are located lower than the insertion-port abutment part 48, the regulating member 42 moves toward the distal end due to the force of gravity applied to the regulating member 42.

In the embodiment, the slider body 45 of the connection slider 41 is adapted to be formed with the locking holes 45d passing through the slider body 45 in the direction of the axis C. However, holes may be formed in the proximal end face of the slider body 45, and the slider abutment parts 49 may be configured to be inserted into the holes.

In the embodiment, the tubular groove 21d of the connecting member 21 is adapted to be formed in the cylindrical shape, and the insertion-port abutment part 48 is adapted to be formed in the cylindrical shape. However, the shapes of the tubular groove 21d and the insertion-port abutment part 48 are not limited to these, and may be tubular shapes. The tubular shape mentioned herein includes not only a shape in which a sectional shape perpendicular to the axis is circular, but also a shape that has an oval or polygonal border.

A rod-like hole extending in the direction of the axis C may be formed in the support face 21b of the connecting member 21, and the insertion-port abutment part may be formed in a rod shape in which the insertion-port abutment part is insertable into the rod-like hole.

In the embodiment, a movement prevention mechanism that prevents the regulating member 42 from moving toward the distal end beyond the connection slider 41 is constituted of the edges of the locking holes 45d of the connection slider 41 and the supports 48d of the regulating member 42. However, the constitution of the movement prevention mechanism is not limited to this.

In the embodiment, the endoscopic treatment device is adapted to be the puncture needle 1. However, the endoscopic treatment device is not limited to the puncture needle 1, and may be, for instance, a ligation device for an endoscope which is used to introduce a snare, forceps, and a clip unit into the human body.

The present invention is not limited by the above description, and is only limited by the scope of the appended claims.

What is claimed is:

1. An endoscopic treatment device comprising:
   an insertion unit configured to be insertable into a channel of an endoscope;
   a manipulation unit provided at a proximal end portion of the insertion unit; and
   a manipulation unit attachment mechanism provided at the manipulation unit, and configured to removably attach the manipulation unit to an insertion port provided at a proximal end portion of the channel of the endoscope when the insertion unit is inserted into the channel of the endoscope,
   wherein the manipulation unit attachment mechanism has:
   a connection slider configured to be engaged with the insertion port by sliding in a first direction intersecting an axis of the insertion unit in a state in which the manipulation unit is attached to the insertion port and be disengaged from the insertion port by sliding in a second direction intersecting the axis of the insertion unit;
   an insertion-port abutment part configured to be movable relative to the connection slider in a direction of the axis of the insertion unit and move toward a proximal end of the insertion unit in the direction of the axis of the insertion unit by coming into contact with the insertion port in the state in which the manipulation unit is attached to the insertion port, wherein
   when insertion port abutment part is disposed in a second position, the manipulation unit is attached to the insertion port, and
   when the insertion port abutment part is disposed in a first position axially displaced in a distal direction from the second position, the manipulation unit is detached from the insertion port; and
   a slider abutment part that is formed at the insertion-port abutment part and that is configured to come into contact with the connection slider to prevent sliding of the connection slider in the first direction when the insertion-port abutment part and the slider abutment part are biased to the first position, and the slider abutment part is configured to not come into contact with the connection slider to permit the sliding of the connection slider in the first direction when the insertion-port abutment part and the slider abutment part are biased to the second position;
   wherein the slider abutment part and the insertion-port abutment part are biased to the first position when the manipulation unit attachment mechanism is not engaged to the insertion port of an endoscope; and
   the slider abutment part and the insertion-port abutment part are biased to the second position when the manipulation unit attachment mechanism is engaged to the insertion port of the endoscope.

2. The endoscopic treatment device according to claim 1, further comprising a biasing member configured to bias the insertion-port abutment part toward the first position.

3. The endoscopic treatment device according to claim 2, wherein:
   the connection slider has a locking hole formed to pass through the connection slider in the direction of the axis; and
   the slider abutment part that has moved to the first position is inserted into the locking hole of the connection slider that has slid in the second direction, and thereby the connection slider is prevented from sliding in the first direction.

4. The endoscopic treatment device according to claim 3, wherein:
   the insertion-port abutment part is formed in a tubular shape;
   a tubular groove is formed in a support face of the manipulation unit, the support face being exposed at a distal end side of the manipulation unit; and
   a proximal end side of the insertion-port abutment part is inserted into the tubular groove.

5. The endoscopic treatment device according to claim 4, wherein:
   the manipulation unit includes a support tube that extends in the direction of the axis and has an outer diameter such that the support tube is insertable into the insertion port; and
   the insertion unit is inserted into the support tube.

6. The endoscopic treatment device according to claim 5, wherein the insertion unit has:
   a sheath; and
   a needle tube configured to be advanceably and retractably inserted into the sheath.

* * * * *